United States Patent [19]

Grant et al.

[11] 4,113,775
[45] Sep. 12, 1978

[54] TRIAMINOGUANIDINIUM SALT OF TETRANITROETHANE

[75] Inventors: Louis R. Grant, Los Angeles; Joseph E. Flanagan, Woodland Hills, both of Calif.

[73] Assignee: Rockwell International Corporation, El Segundo, Calif.

[21] Appl. No.: 732,624

[22] Filed: Oct. 15, 1976

[51] Int. Cl.$^2$ ............................................. C07C 133/10
[52] U.S. Cl. .................................. 260/564 G; 149/92; 260/644
[58] Field of Search ............... 260/564 R, 564 G, 644; 149/92

[56] References Cited

U.S. PATENT DOCUMENTS 2,963,507  12/1960  Rudner et al. ................... 260/644 X

*Primary Examiner*—Leland A. Sebastian
*Attorney, Agent, or Firm*—L. Lee Humphries; Robert M. Sperry

[57] ABSTRACT

An energetic salt of tetranitroethane and triaminoguanidine which can be used as a high energy solid propellant oxidizer.

5 Claims, No Drawings

TRIAMINOGUANIDINIUM SALT OF TETRANITROETHANE

BACKGROUND OF THE INVENTION

1. Field of the Invention

This invention relates to compositions of matter and methods of producing the same and is particularly directed to bis-triaminoguanidinium tetranitroethane and a method of producing this compound.

2. Description of the Prior Art

From U.S. Pat. No. 3,257,470, there is known a process for preparing the diammonium salt of 1, 1, 2, 2-tetranitroethane. However, in the solid propellant art, there is a continual search for compositions which are capable of yielding still greater energy. Thus, it would be apparent to one skilled in this art that a triaminoguanidinium salt, if such existed, would be desirable since it would be more energetic than the diammonium salt taught by the aforementioned patent. Unfortunately, no such triaminoguanidinium salt was known in the prior art. Furthermore, attempts to produce a triaminoguanidinium salt by the method of the foregoing patent were unsuccessful.

BRIEF SUMMARY AND OBJECTS OF THE INVENTION

The disadvantages of the prior art are overcome with the present invention and a triaminoguanidinium salt of tetranitroethane is disclosed as a high energy oxidizer, together with an ion-exchange method of producing the same.

Accordingly, it is an object of the present invention to provide an improved oxidizer composition, together with a method for producing the same.

Another object of the present invention is to provide an oxidizer composition which is capable of yielding greater energy than those of the prior art, together with a method of producing the same.

An additional object of the present invention is to provide a triaminoguanidinium salt of tetranitroethane.

A further object of the present invention is to provide an ion-exchange method for producing a triaminoguanidinium salt of tetranitroethane.

A specific object of the present invention is to provide bis-triaminoguanidinium salt of tetranitroethane, together with an ion-exchange method for producing the same.

These and other objects and features of the present invention will be apparent from the following detailed description.

DETAILED DESCRIPTION OF THE INVENTION

In accordance with the present invention, bis-triaminoguanidinium tetranitroethane (BTATN) is proposed as a highly energetic oxidizer composition and an ion-exchange method for producing the new composition is disclosed. Twenty grams of Dowex 50-X8 (total exchange capacity, 94 milliequiv., an ion exchange resin available commercially from Dow Chemical Company), were slurried in water and transferred to a 50 ml buret. The ion exchange resin was then treated with 100 ml of 5% HCl in the conventional fashion to ensure the resin being in the acid form. The resin was subsequently washed with water until the eluate was neutral to pH paper. Dried triaminoguanidine (1.598 grams, 15.3 mmoles), prepared by precipitation with dimethylformamide from an aqueous reaction mixture of sodium hydroxide and triaminoguanidinium nitrate, was dissolved in 20 ml of water in a 500 ml Erlenmeyer flask. A nitrogen purge was maintained over the triaminoguanidine solution during reaction. Dipotassium tetranitroethane (2.012 grams, 7.0 mmoles) was dissolved in 300 ml of water and the resulting solution was passed over the ion exchange resin. The eluate was added directly to the triaminoguanidine solution with stirring. This highly dilute solution of $K_2C_2N_4O_8$ allowed its conversion to $H_2C_2N_4O_8$ without any evidence of gross decomposition (gassing) of the acid. The basic amine solution became reddish-orange on addition of the eluate. At the point where nearly all of the $K_2C_2N_4O_8$ solution had been added to the buret, the reaction mixture became neutral to pH paper. Also, there was a color change from a reddish-orange to a very light yellow color. Addition of $H_2C_2N_4O_8$ was stopped at this point.

The slightly turbid solution was stirred for an aditional hour, filtered, and the filtrate was concentrated on a rotary evaporatory using a water aspiration pump and a water bath heated at 40° to 45° C. After evaporation to dryness, the filtrate yielded 3.04 grams of a reddish-orange solid. This solid was washed from the evaporation flask with absolute methanol and filtered. The recovered solid (2.10 grams after drying in vacuo at ambient temperature) was light yellow and the filtrate was reddish-orange.

The reaction product melted at 123° to 125° C (decomposition) and its infrared spectrum showed bands typical of those for triaminoguanidinium salts. Water bands were also present. A portion of the product was added to an Abderhalden Pistol and heated in vacuo with refluxing chloroform (B.P. 61° C) for 19 hours. An infrared spectrum of the sample in a KBr pellet showed an absence of $H_2O$ bands, and there was no change in melting point (123° to 125° C). Elemental analysis confirmed that the product was BTATN.

A state-of-the-art compound, ethylendinitramine, has a specific impulse value of 244 seconds, whereas the new compound yields a specific impulse value of 253 seconds. Thus, BTATN is a highly energetic oxidizer composition for solid propellants.

Obviously, numerous variations and modifications may be made without departing from the present invention. Accordingly, it should be clearly understood that the form of the present invention described above is illustrative only and is not intended to limit the scope of the present invention.

We claim:

1. An energetic composition consisting of a triaminoguanidinium salt of tetranitroethane.
2. The composition of claim 1 wherein:
   said salt is bis-triaminoguanidinium tetranitroethane.
3. The composition of claim 1 wherein:
   said salt has the formula $C_4H_{18}N_{16}O_8$.
4. A method for producing bis-triaminoguanidinium tetranitroethane comprising the steps of:
   establishing an ion-exchange mechanism between triaminoguanidine and dipotassium tetranitroethane.
5. The method of claim 4 wherein said establishing step comprises:
   preparing the acid from of an ion-exchange resin;
   washing said resin with water until the eluate has neutral pH,
   preparing an aqueous solution of triaminoguanidine,
   preparing an aqueous solution of dipotassium tetranitroethane,
   passing said dipotassium tetranitroethane solution over said ion-exchange resin, and
   mixing the resulting tetranitroethane solution with the triaminoguanidine solution.

* * * * *